United States Patent [19]

Clark et al.

[11] 4,441,911
[45] Apr. 10, 1984

[54] HERBICIDAL HETEROCYCLIC PENTALENES

[75] Inventors: Michael T. Clark; Ian J. Gilmore, both of Sittingbourne, England

[73] Assignee: Shell Oil Company, Houston, Tex.

[21] Appl. No.: 418,370

[22] Filed: Sep. 15, 1982

Related U.S. Application Data

[63] Continuation-in-part of Ser. No. 388,777, Jun. 15, 1982, abandoned.

[30] Foreign Application Priority Data

Jun. 24, 1981 [GB] United Kingdom ............... 8119403

[51] Int. Cl.³ .................. A01N 43/02; C07D 291/08
[52] U.S. Cl. ......................................... 71/91; 71/90; 548/122
[58] Field of Search ...................... 71/90, 91; 548/122

[56] References Cited

U.S. PATENT DOCUMENTS

| 3,182,068 | 5/1965 | Sasse et al. | 548/122 |
| 4,179,441 | 12/1979 | Moore | 71/90 |
| 4,289,524 | 9/1981 | Belkind | 71/90 |

OTHER PUBLICATIONS

Perrier et al., "Sulfur—Containing, etc.," (1979), CA 91, No. 74534c, (1979).

Primary Examiner—Glennon H. Hollrah

[57] ABSTRACT

Herbicidal heterocyclic pentalenes of the formula:

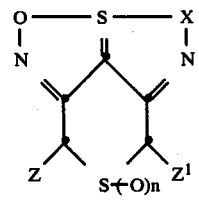

wherein the symbols have assigned meanings.

3 Claims, No Drawings

HERBICIDAL HETEROCYCLIC PENTALENES

This application is a continuation-in-part of application Ser. No. 388,777, filed on June 15, 1982, now abandoned.

DESCRIPTION OF THE INVENTION

It has been found that certain oxadithiadiaza- and oxathiaoxadiaza-2,5-pentalenes have useful herbicidal properties. These compounds are characterized by the general formula:

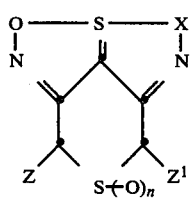

wherein X is O or S, Z and $Z^1$ each is hydrogen or alkyl of from one to three carbon atoms, and n is zero, one or two, with the proviso that when X is sulfur, n is zero.

The invention also provides a process for the preparation of compounds of Formula I which comprises treating a dioxime of the general formula

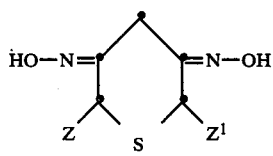

with sulphur monochloride and/or sulphur dichloride. The product of this reaction is typically a mixture of the desired oxadiathiadiaza-2,5-pentalene of Formula I (the compound wherein X is a sulphur atom) and the desired oxathiaoxadiaza-2,5-pentalene of Formula I (the compound wherein X is an oxygen atom). The ratio in which these two products form during the reaction is rather variable depending on the chemical make up of the dioxime starting material used and the type of sulphur chloride employed. Typically when sulphur dichloride is used rather than sulphur monochloride, the yield of oxathiaoxadiaza-2,5-pentalene is enhanced. The reaction is suitably conducted in a polar organic solvent such as tetrahydrofuran or diethyl ether, which is inert under the reaction conditions employed. The reaction temperature will typically range between −80° and −20° C. When the reaction is carried out in batch fashion it is desirable to slowly add the sulphur chloride reactant to the dioxime in the polar organic solvent at a temperature of from −80° to −20° C., to maintain this temperature for a time interval, for example 8 to 12 hours, and then to allow the reaction mixture to warm slowly to ambient temperature (20° C.), holding it at this temperature for an additional 6 to 16 hours. Generally the total reaction time will range between 16 and 30 hours.

As noted previously, the reaction product of the reaction between the dioxime of Formula II and a sulphur chloride generally contains a mixture of the two compounds of Formula I which are identical in structure except for the nature of the X substituent. The desired oxadithiadiaza-2,5-pentalene component and the oxathiaoxadiaza-2,5-pentalene component are suitably separated from the mixed reaction product using conventional techniques. In a preferred separation process, the two components in the reaction product are isolated by chromatography on silica using an eluant such as petroleum/ether or methylene chloride. After isolation, the components can be further purified using conventional solvent recrystallization techniques, alcohols such as ethanol and hydrocarbon solvents such as hexane, cyclohexane and benzene being suitable recrystallization solvents.

The dioximes of Formula II are generally known compounds, being prepared by reaction of the appropriate beta-diketone of the formula

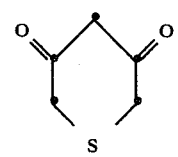

with hydroxylamine. This reaction is typically carried out by reacting stoichiometric amounts of the diketone (1 mole) and hydroxylamine (2 moles) at temperatures from 25° to 100° C. for 10 to 60 minutes in a polar solvent.

The precursor β-diketones (IV) are also known compounds: Terasawa, Tadao, Okada, and Toshihiko, Journal of Organic Chemistry, volume 42, pages 1163–1169 (1977).

Compounds of Formula I wherein n is one or two, respectively, can be prepared by treating the corresponding compound of Formula I wherein n is zero with one, or two, equivalents of meta-chloroperbenzoic acid, respectively.

Preparation of typical individual species of the compounds of Formula I in particular instances is described in the following examples. In each case, the identity of each product and each intermediate was confirmed by appropriate chemical and spectral analyses. In these examples, the compounds are identified in terms of the symbols set out in the definition:

EXAMPLE 1

Compound 1 (Formula I, X=O, Z=H, $Z^1$=H, n=zero)

Compound 2 (Formula I, X=S, Z=H, $Z^1$=H, n=zero)

31.4 g of sulfur dichloride (filtered through glass wool to remove any elemental sulfur) was added drop-by-drop to a suspension of 22.4 g of thiacyclohexane-3,5-dione dioxime in 600 ml of dry tetrahydrofuran, at −65° C. The resulting mixture was stirred at that temperature for 12 hours, then allowed to warm to room temperature and poured into water. The resulting mixture was extracted with chloroform. The extract was dried (Na₂SO₄), the solvent was evaporated and the residue was chromatographed over silica gel, methylene chloride being used as the eluant. The first fraction, sulfur, was discarded. The second fraction, orange green in color, was recrystallized from ethanol to give 1, as greenish-yellow needles, m.p.: 97°–99° C. On work-up in the same manner, the third fraction, orange-brown in color, gave 2, as black needles, m.p.: 138°–140° C.

Treatment of the dioxime with sulfur monochloride and work-up of the products by the same procedure gave 1, m.p.: 99° C., and 2, m.p.: 141° C.

EXAMPLE 2

By the same procedures described in Example 1, there were prepared the following further compounds of Formula I:

Compound 3 (Formula I, X=O, Z=H, $Z^1$=isopropyl, n=zero), as an oil.

Compound 4, (Formula I, X=S, Z=H, $Z^1$=isopropyl, n=zero), as an oil.

Compound 5, (Formula I, X=S, Z=isopropyl, $Z^1$=H, n=zero), as a solid, m.p.: 76° C.

EXAMPLE 3

Compound 6 (Formula I, X=O, Z=H, $Z^1$=H, n=one)

A solution of 1.1 g of meta-chloroperbenzoic acid in dry methylene chloride was added to a solution of 0.95 g of 1 in dry methylene chloride, at room temperature, and the resulting mixture was stirred at room temperature for 15 minutes. The mixture was washed with saturated sodium bicarbonate solution. The methylene chloride phase was dried ($Na_2SO_4$), the solvent was evaporated and the residue was recrystallized from methanol to give 6, as organic needles, m.p.: 183°–184° C.

EXAMPLE 4

Compound 7 (Formula I, X=O, Z=H, $Z^1$=H, n=two)

7 was obtained, as pale orange needles, m.p.: 167°–168° C., by the procedure described in Example 3, except using double the amount of meta-chloroperbenzoic acid.

The compounds of Formula I have useful herbicidal properties and the invention provides a method for combating undesired plant growth at a locus, which comprises applying to the locus, an effective dosage of a compound of Formula I. Likewise, the invention includes plant growth control compositions comprising an inert carrier or a surface-active agent, or both a carrier and a surface-active agent, and as active ingredient at least one compound of Formula I.

A carrier in a composition according to the invention is any material with which the active ingredient is formulated to facilitate application to the locus to be treated, which may for example be a plant seed or soil, or to facilitate storage, transport or handling. A carrier may be a solid or a liquid, including a material which is normally gaseous but which has been compressed to form a liquid, and any of the carriers normally used in formulating herbicidal compositions may be used.

Suitable solid carriers are natural and synthetic clays and silicates, for example, natural silicas such as diatomaceous earth; magnesium silicates, for example, talcs, magnesium aluminum silicates, for example, attapulgites and vermiculites; aluminum silicates, for example, kaolinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example coumarone resins, polyvinyl chloride and styrene polymers and copolymers; bitumen, waxes such as, for example, beeswax, paraffin wax, and chlorinated minerals waxes; and solid fertilizers, for example, superphosphates.

Examples of suitable fluid carriers are water, dimethyl sulfoxide, alcohols, such as, for example, methanol, isopropyl alcohol, glycols; ketones such as for example, acetone, methyl ethyl ketone, methyl isobutyl ketone, isophorone and cyclohexanone; ethers such as, for example, cellosolves; aromatic hydrocarbons such as, for example, benzene, toluene and xylene; petroleum fractions such as, for example, herosene, light mineral oils; chlorinated hydrocarbons, such as, for example, carbon tetrachloride, perchloroethylene, trichloroethane, including liquefied normally vaporous gaseous compounds. Mixtures of different liquids are often suitable. The surface-active agent may be an emulsifying agent or a dispersing agent or a wetting agent; it may be nonionic or ionic any of the surface-active agents usually applied in formulating herbicides or insecticides may be used. Examples of suitable surface-active agents are sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil and sodium alkyl-aryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 or 75% by weight of toxicant and usually contain in addition to solid carrier, 3–10% by weight of a dispersing agent, 15% of per volume of appropriate additives such as stabilizers, penetrants and corrosion inhibitors. Suspension concentrates are compounded so as to obtain a stable, non-sedimenting flowable product and usually contain 10–75% weight toxicant, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also like within the scope of the present invention. The said emulsions may be of the water-in-oil or of the oil-in-water type, and may have a thick mayonnaise-like consistency.

The compositions may also contain other ingredients, for example, other compounds possessing pesticidal, especially insecticidal, acaricidal, herbicidal or fungicidal properties.

Protection of a locus or area from unwanted plants is effected by applying a compound of Formula I, ordinarily in a composition of one of the aforementioned types, to the soil in which seeds of the unwanted plants are present, or to the foliage of the plants. The active compound, of course, is applied in an amount sufficient to exert the desired action.

The amount of the compound of Formula I to be used in controlling undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.02 to 10.0, preferably from 0.1 to 5.0, kilograms per hectare of the compound of Formula I will be satisfactory.

Herbicidal Activity

To evaluate their herbicidal activity in compositions according to the invention, compounds of the previous examples were tested using as a representative range of plants: maize, *Zea mays* (MZ); rice, *Oryza sativa* (R); barnyard grass, *Echinochloa crusgalli* (BG); oat, *Avena sativa* (O); linseed, *Linum usitatissimum* (L); mustard, *Sinapis alba* (M); sugar beet, *Beta vulgaris* (SB) and soya bean, *Glycine max* (S).

The tests fall into two categories, preemergence and postemergence. The preemergence tests involved spraying a liquid formulation of the compound onto the soil in which the seeds of the plant species mentioned above had recently been sown. The postemergence tests involved two types of test, viz., soil drench and foliar spray tests. In the soil drench tests the soil in which the seedling plants of the above species were growing, was drenched with a liquid formulation containing a compound of the invention, and in the foliar spray tests the seedling plants were sprayed with such a formulation.

The soil used in the tests was a prepared horticultural loam.

The formulations used in the tests were prepared by diluting with water, solutions of the test compounds in acetone containing 0.4% by weight of an alkylphenol-/ethylene oxide condensate available under the trade name Triton X-155. The acetone solutions were diluted with water and the resulting formulations applied typically at dosage levels corresponding to 5 kg and/or 1 kg of active material per hectare in a volume equivalent to 650 liters per hectare in the soil spray and foliar spray tests, and at a dosage level equivalent to 10 kilograms of active material per hectare in a volume equivalent to approximately 3,000 liters per hectare in the soil drench tests.

In the preemergence tests untreated sown soil and in the postemergence tests untreated soil bearing seedlings plants were used as controls.

The herbicidal effects of the test compounds were assessed visually eleven days after spraying in the foliage and drenching the soil and twelve days after spraying the soil, and were recorded on a 0–9 scale. A rating 0 indicates growth as untreated control, a rating 9 indicates death. An increase of 1 unit on the linear scale approximately to a 10% increase in the level of effect.

The results of the tests are set out in Table I.

TABLE I

| Compound No. | Soil Drench 10 kg/ha | | | | | | | | Dosage kg/ha | Foliar Spray | | | | | | | | Preemergence | | | | | | | |
|---|---|---|---|---|---|---|---|---|---|---|---|---|---|---|---|---|---|---|---|---|---|---|---|---|---|
| | MZ | R | BG | O | L | M | SB | S | | MZ | R | BG | O | L | M | SB | S | MZ | R | BG | O | L | M | SB | S |
| 1 | 8 | 9 | 9 | 8 | 9 | 9 | 9 | 9 | 5 | 8 | 9 | 9 | 8 | 9 | 9 | 9 | 9 | 8 | — | 9 | 7 | 7 | 9 | 9 | 8 |
| | | | | | | | | | 1 | 5 | 8 | 9 | 6 | 8 | 9 | 9 | 8 | 5 | — | 8 | 5 | 5 | 8 | 8 | 4 |
| 2 | 0 | 0 | 0 | 0 | 0 | 0 | 0 | 0 | 5 | 3 | 6 | 8 | 4 | 9 | 9 | 9 | 6 | 3 | — | 3 | 0 | 0 | 3 | 4 | 0 |
| | | | | | | | | | 1 | 1 | 5 | 7 | 4 | 9 | 9 | 9 | 5 | 0 | — | 0 | 0 | 0 | 1 | 2 | 0 |
| 3 | 8 | 6 | 9 | 8 | 9 | 9 | 9 | 8 | 5 | 7 | 6 | 9 | 8 | 9 | 9 | 9 | 9 | 5 | 7 | 9 | 7 | 9 | 8 | 8 | 4 |
| | | | | | | | | | 1 | 2 | 2 | 8 | 5 | 7 | 9 | 8 | 8 | 3 | 3 | 8 | 3 | 6 | 6 | 6 | 3 |
| 4 | 0 | 0 | 2 | 0 | 4 | 0 | 3 | 2 | 5 | 4 | 9 | 6 | 6 | 8 | 9 | 9 | 9 | 0 | 0 | 0 | 0 | 0 | 0 | 0 | 0 |
| | | | | | | | | | 1 | 2 | 4 | 4 | 3 | 7 | 9 | 9 | 8 | 0 | 0 | 0 | 0 | 0 | 0 | 0 | 0 |
| 5 | 0 | 0 | 0 | 0 | 0 | 0 | 0 | 0 | 5 | 5 | 5 | 6 | 5 | 8 | 9 | 9 | 9 | 0 | 0 | 0 | 0 | 0 | 0 | 0 | 0 |
| | | | | | | | | | 1 | 3 | 3 | 4 | 2 | 7 | 9 | 8 | 5 | 0 | 0 | 0 | 0 | 0 | 0 | 0 | 0 |
| 6 | 7 | 8 | 9 | 7 | 9 | 9 | 9 | 9 | 5 | 8 | 9 | 9 | 8 | 9 | 9 | 9 | 9 | 8 | — | 9 | 7 | 6 | 8 | 8 | 0 |
| | | | | | | | | | 1 | 6 | 7 | 9 | 5 | 7 | 9 | 9 | 8 | 6 | — | 9 | 5 | 2 | 5 | 4 | 0 |
| 7 | 8 | 5 | 6 | 8 | 7 | 9 | 0 | 9 | 5 | 7 | 8 | 9 | 8 | 9 | 9 | 9 | 9 | 3 | — | 7 | 3 | 4 | 7 | 0 | 0 |
| | | | | | | | | | 1 | 4 | 6 | 8 | 6 | 8 | 9 | 5 | 7 | 3 | — | 5 | 2 | 0 | 3 | 0 | 0 |

We claim:

1. A compound of the formula

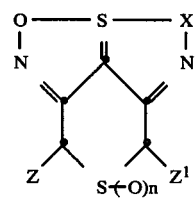

wherein X is O or S, Z and $Z^1$ each is hydrogen or alkyl of from one to three carbon atoms, and n is zero, one or two, with the proviso that when X is sulfur, n is zero.

2. A method for controlling unwanted plant growth at a locus, which comprises treating the locus with an effective dosage of a compound of claim 1.

3. A herbicidal composition comprising an effective amount of a compound of claim 1 together with an inert carrier, a surface-active agent, or both.

* * * * *